(12) United States Patent
Krause et al.

(10) Patent No.: US 8,607,639 B2
(45) Date of Patent: Dec. 17, 2013

(54) METHOD AND DEVICE FOR DETERMINING MECHANICAL STRESS LOAD AND INTERFACE EFFECTS ON PARTICLES DISPERSED IN A FLUID

(75) Inventors: Hans-Jürgen Krause, Grünstadt (DE); Carsten Weber, Maxdorf (DE); Sonja Simon, Erlangen (DE); Wolfgang Peukert, Mark Schwaben (DE)

(73) Assignees: AbbVie Deutschland GmbH & Co. KG, Wiesbaden (DE); Friedrich-Alexander-Universitat Erlangen-Nurnberg, Erlangen (DE)

( * ) Notice: Subject to any disclaimer, the term of this patent is extended or adjusted under 35 U.S.C. 154(b) by 337 days.

(21) Appl. No.: 13/049,362

(22) Filed: Mar. 16, 2011

(65) Prior Publication Data

US 2012/0031191 A1 Feb. 9, 2012

Related U.S. Application Data

(60) Provisional application No. 61/314,488, filed on Mar. 16, 2010.

(30) Foreign Application Priority Data

Mar. 16, 2010 (EP) .................................... 10156692

(51) Int. Cl.
*G01N 3/00* (2006.01)
(52) U.S. Cl.
USPC .......................................................... 73/760
(58) Field of Classification Search
USPC .......................................................... 73/760
See application file for complete search history.

(56) References Cited

U.S. PATENT DOCUMENTS

| | | | | |
|---|---|---|---|---|
| 3,478,559 A | * | 11/1969 | Polakowski | 72/241.6 |
| 3,743,404 A | * | 7/1973 | Zucker | 399/131 |
| 5,048,762 A | * | 9/1991 | Landa et al. | 241/21 |
| 7,112,452 B2 | * | 9/2006 | Cho et al. | 436/518 |
| 7,916,289 B2 | * | 3/2011 | Heinzelmann et al. | 356/244 |
| 2008/0246945 A1 | | 10/2008 | Heinzelmann et al. | |

OTHER PUBLICATIONS

Taylor, G.I., "The formation of emulsions in definable fields of flow," Proc. Roy. Soc. London Ser. A, 146, 501 (1934).
Lagnado, R.R., et al., "Visualization of three-dimensional flow in a four-roll mill," Experiments in Fluids, 9, pp. 25-32 (1990).

* cited by examiner

*Primary Examiner* — Lisa Caputo
*Assistant Examiner* — Octavia Davis-Hollington
(74) *Attorney, Agent, or Firm* — Lisa V. Mueller; Michael Best & Friedrich LLP (57) ABSTRACT

The present invention concerns a method and a device for determining mechanical stress load, and optionally interface effects, on particles dispersed in a fluid. According to the invention, fluid comprising dispersed particles such as biomolecules is fed into a sample space of a device comprising a jacket which encloses a sample chamber and at least two rolls arranged within said jacket such that said sample space is defined between said rolls, said rolls being independently rotatable with respect to each other, wherein said jacket has an inner surface which is essentially adapted to the outer surface of the rolls, rotational movement is imparted to at least one of the rolls of said device, and changes in the state of said particles are determined from which mechanical stress load acting on the particles can be determined.

26 Claims, 9 Drawing Sheets

METHOD AND DEVICE FOR DETERMINING MECHANICAL STRESS LOAD AND INTERFACE EFFECTS ON PARTICLES DISPERSED IN A FLUID

CROSS-REFERENCE TO RELATED APPLICATIONS

This claims priority to U.S. Provisional Patent Application No. 61/314,488, filed on Mar. 16, 2010, and European Patent Application No. 10156692.5, filed on Mar. 16, 2010, the contents of all of which are hereby incorporated by reference.

DESCRIPTION

1. Technical Field

The present invention relates to a method and a device for determining mechanical stress load, and optionally interface effects, on particles dispersed in a fluid, especially to a method and a device where said dispersed particles comprise biomolecules.

2. Background

In many industrial biotechnological processes, biomolecules dispersed in fluids, typically liquids, are subject to mechanical stress at various stages of manufacturing, purification, formulation and packaging processes. For instance, fluids containing biomolecules are stirred, pumped, passed through filters, transferred through pipes from one process section to a subsequent process section, etc. Typical mechanical stresses imparted on the biomolecules include shear stress, rotational stress and extensional stress. In addition, the biomolecules can interact with interfaces, typically liquid/solid-interfaces, such as surfaces of pipes and filters, or liquid/gas-interfaces, such as liquid surfaces or surfaces of gas bubbles dispersed in the liquid.

It is known that mechanical stress acting on biomolecules can result in a degradation of the biomolecules, caused for instance by the formation of larger aggregates, by disintegration into smaller particles or by structural changes such as an unfolding of one or more substructures of the biomolecules. As these degradation processes caused by mechanical stress strongly affects the biological activity of the final product, it is important to ensure that mechanical stresses imparted on the biomolecules during industrial biotechnological processes does not exceed certain acceptable limits.

In the past, the degradation of proteins due to mechanical stress was usually mainly investigated in the equipment, which was actually used in the industrial processes such as stirred tank reactors, pumps, capillaries, filters, etc. However, these investigations suffer from the drawback that the fluid flows occurring in such devices, are rather undefined so that no systematic analysis of the impact of various forms of mechanical stress on the degradation of biomolecules could be performed. Moreover, very large sample volumes are required when using conventional industrial equipment, even when using devices reduced to laboratory scale instead of production scale equipment. Moreover, a downscaling is not always feasible as surface effects will be more dominant on laboratory scale than on production scale.

In order to allow a systematic, reproducible collection of data on the correlation between shear stress and stability of proteins dispersed in a solution, patent application US 2008/0246945 A1 describes an apparatus for quantifying shear stress on a formulation comprising biomolecules. The known apparatus comprises two syringes which are connected to each other via a defined cannula. The diameter of the cannula and the volumetric flow of the protein solution allows to exert a defined shear stress on the proteins in the solution. This device suffers from the drawback, however, that only shear stress effects on protein degradation can be investigated. In addition, the known device can hardly be adapted to inline measurement of particle characteristics in the fluid.

It is therefore an object of the present invention to provide a method and a device for determining mechanical stress load on particles, in particular biomolecules, dispersed in a fluid, which allows to determine the effect of various types of mechanical stress on the degradation of the dispersed particles, in particular via inline measurement.

It is also known that different types of fluidic flow patterns can be generated in a gap between two or more rolls, which are arranged adjacent to each other and which are rotated in the same or in opposite directions. For instance, the generation of extensional flows was first described in 1934 in G. I. Taylor, *The formation of emulsions in definable fields of flow*, Proc. Roy. Soc. London Ser. A, 146, 501 (1934), using a so-called four-roll mill Such devices are frequently used to investigate physical phenomena such as the deformation, break-up and coalescence of fluidic drops, the rheology of viscoelastic fluids, conformational changes of macromolecules induced by fluid flows, shear-induced crystallization of polymers and the investigation of deoxy-ribonucleic acid (DNA) in flow.

It has, however, not been suggested to use such roll devices to investigate the degradation of biomolecules caused by mechanical stress.

SUMMARY OF THE INVENTION

The present invention suggests to use the concept to generate defined types of mechanical stress in a fluid known from the four-roll mill in order to determine mechanical stress load on particles dispersed in a fluid, in particular biomolecules dispersed in a fluid.

The present invention therefore concerns a method for determining shear stress load on particles dispersed in a fluid, comprising the steps of feeding fluid into a sample space of a device comprising a jacket which encloses a sample chamber and at least two rolls arranged within said jacket such that said sample space is defined between said rolls, said rolls being independently rotatable with respect to each other, wherein said jacket has an inner surface which is essentially adapted to the outer surface of the rolls, imparting rotational movement to at least one of said rolls of said device, determining changes in the state of said particles.

Accordingly, the present invention also concerns a device for determining mechanical stress load on particles dispersed in a fluid comprising a jacket which encloses a sample chamber and at least two rolls arranged within said jacket such that a sample space is defined between said rolls, said rolls being independently rotatable with respect to each other, e.g. using a separate motor to drive each roll. In the device of the present invention the jacket has an inner surface which is essentially adapted to the outer surface of the rolls as to form a closely fitting envelope around the outer profile of the roll arrangement.

As the profile of the inner surface of the jacket is adapted to the envelope profile of the roll assembly, the total sample volume required to fill the device of the present invention can be minimized. Moreover, stagnant areas (dead spots) in the fluid flow pattern can be avoided.

To be more specific, according to the present invention, the inner surface of the jacket is adapted in such a way to the outer surface of the rolls that on a certain angular section of each roll, an essentially constant gap between the outer surface of each roll and the adjacent inner surface of the jacket is maintained. For a two-roll mill, said angular section of each roll is preferably extends over an angular range of at least 180° and may extend over an angular range of up to approximately 280°. For a four-roll mill, said angular section of each roll is preferably extends over a range of at least 90° and may extend over a range of up to approximately 180°. Thus, for a four-roll device, a specific shape of the jacket is obtained which resembles a cloverleaf shape. This shape not only allows to reduce the sample volume required but also avoids dead spots in the fluid flow.

The absolute size of the device of the present invention may vary depending on the specific requirements of certain investigations. Thus, while the device may be designed as small as to house a total sample volume in the range of several microliters using e.g. micromachining techniques, wall and surface effects will tend to play an ever increasing roll. Thus, sample volumes in the range of several milliliters are currently preferred as this range appears to be an acceptable compromise between avoiding wall and surface effects and saving expensive protein solutions. Further, a fluid volume in the range of micro-liters is usually sufficient for a broad analysis of the sample during or after the mechanical stress impact.

Furthermore the dimensions of the jacket should allow optical entries of 250 μm in order to use e.g. glass fibers for optical analytical measurements.

The jacket and the rolls are preferably made of a material which is inert with respect to the particles to be tested such as stainless steel, or stainless steel coated with a fluoropolymer such as perfluoroalkoxy (PFA) or polytetrafluoroethylene (PTFE). The wall may also be coated for instance using a matrix of polyethylene glycol which would be particularly an advantage in the micro-liter volume range.

Although rolls having a variety of shapes, for instance a conical or frusto-conical shape, can be used, according to a first preferred embodiment of the present invention said rolls are essentially cylindrical rolls. In this event, the inner surface of said jacket has at least partially an essentially cylindrical shape having a second radius of a curvature which is slightly larger than said first radius of a curvature of the cylindrical rolls. Said second radius of curvature is preferably selected such that said predefined gap between the outer surface of the rolls and the inner surface of the jacket is obtained over the above mentioned angular range, where the jacket has a cylindrical shape.

Preferably, all rolls of the device are essentially identical and have a similar first radius of a curvature.

While the device of the present invention can house any number of two or more rolls, a device having four rolls is particularly preferred. Such a four-roll device can establish well-defined flow patterns in the sample space between the rolls, which allow to selectively impart either of rotational stress, shear stress or extensional stress onto particles comprised in a fluid present in said sample space. As defined mechanical stress in homogeneous two-dimensional flow patter can be imparted on the particles, a relation between the applied stress and the "response" of the particles can be established. According to the corresponding method of the present invention, the rolls are rotated such as to impart at least one of rotational stress, shear stress and extensional stress on the particles. For instance, in a four-roll device having a rolls centered on each corner of a square, rotational stress can be imparted on the particles, if all four rolls are rotated in the same direction with essentially the same angular speed. Shear stress can be imparted on the particles by rotating two diagonally opposing rolls in opposite directions and leaving the neighboring rolls at rest. Extensional stress can be exerted on the particles by rotating all four rolls such that each neighboring rolls are rotated in opposite directions. Usually, a superposition of rotational, shear and extensional stress is imparted on the particles but the device of the present invention allows to emphasis the effect one or more of these stress modes on the particles.

Although in the sample space defined between the rolls, rotational stress, shear stress or extensional stress an selectively be imparted on the particles dispersed in the fluid, there will always be some shear stress effected on the particles in the gap between a rotating roll and the jacket. However, it has surprisingly been found that this shear stress does not significantly exceed the shear stress present at the surface of a rotating roll alone so that the influence of the gap is in many cases negligible. Moreover, it possible to compensate for the shear stress effects of the gap when evaluating the measurement results.

According to a further embodiment, the device of the present invention also comprises means for determining changes in the state of said particles dispersed in said fluid. Changes in the state of the particles may for instance be determined by directly measuring properties of the particles or indirectly by measuring properties of the fluid in which the particles are dispersed or by a combination of these methods. Suitable techniques include turbidity measurements, light extinction, single particle counting, dynamic light scattering, fluorescence spectroscopy, absorption spectroscopy, UV/VIS spectroscopy, IR spectroscopy, light microscopy, flow-field fractioning, imaging techniques, for instance CCD imaging, etc. The means for determining changes in the state of the particles can be arranged for online or offline measurement. Also online and offline analytical methods may advantageously be combined.

When using online analytical methods for in-situ analysis, the jacket may comprise one or more optical windows for transmitting light into and from the sample space. Alternatively or in addition, the bottom or lid of the sample space may transparent or comprise an optical window.

Preferably, the device of the present invention further comprises means for controlling the temperature of the fluid in the sample chamber. To this effect, water or any other suitable heat transfer medium which has been heated or cooled to a selected temperature may be passed through the jacket of the device. Alternatively, the jacket may be heated or cooled using for instance thermoelectric devices.

If it is desired to avoid effects at the liquid/air interface on the surface of the sample space, the device of the present invention is provided with a lid which is preferably made from an inert material. The lid can be transparent or can be provided with a transparent window to allow measurements being made from above the sample space.

If it is desired to investigate the effect of defined liquid/gas interfaces on the stability of the particles dispersed in the fluid, the lid may be configured as a sort of hood so as to define a gas space over said sample space. The lid may comprise means for feeding and discharging gas to and from the gas space to allow for an exchange of gas or even for the generation of a continuous gas flow.

According to one embodiment, a defined fluid volume is fed into the sample space and at least one roll of the device of the present invention is rotated for a predetermined time Inline measurements of changes of the state of the particles can be performed while said at least one roll is rotated or after said predetermined time has elapsed. In addition to inline measurements, small samples of the fluid in the sample space may be withdrawn for offline analysis or the whole fluid volume may be used for offline analysis once the application of mechanical stress has been completed.

In another embodiment of the present method, fluid is continuously passed through the sample space so that the mechanical stress imparted on the particles is determined by the rotational speed and direction of the rolls and the volumetric flow of the fluids through the sample space. E.g. fluid may enter the sample chamber via feed ducts arranged in the lid of the device and may leave the sample chamber via discharge ducts arranged in the bottom of the device. Feed and discharge ducts may also bee used to fill a batch volume of the fluid into the sample chamber and to purge the sample chamber with one more cleaning fluids between the analysis of subsequent samples. In this embodiment, the means for determining changes in the state of the particles are preferably arranged downstream of the sample space. Accordingly, the measurement of changes in the state of the particles is not hindered by the rolls of the device so that a larger variety of measurement tools analytical tools can be employed.

Preferably, however, the means for determining changes in the state of the particles are arranged such that said changes of the state of the particles can be determined via inline measurement within the sample space of the device, even during operation of the rolls.

According to a preferred method of the invention, the particles dispersed in the fluid comprise biomolecules, in particular high molecular weight biomolecules such as proteins (e.g. enzymes or antibodies) or nucleic acids (e.g. DNA or RNA).

The method of the present invention may find various applications in biotechnology. For instance, the method of the invention may be used to determine a maximum tolerable stress load on the biomolecules.

The maximum tolerable stress load may be used in the design of a plant for processing biomolecules, in particular in the configuration of pumps, filters, pipe sections, etc. Accordingly, the present invention also relates to a plant for processing biomolecules dispersed in a fluid, wherein said plant is designed such that the stress load acting on the biomolecules does not exceed a maximum tolerable stress load as determined with the method of the present invention. This provides an essential advantage during the development and production of e.g. therapeutic proteins since the molecules can be tested with regard to their stress resistance in the laboratory scale. With the date obtained in the laboratory, critical process steps of the manufacturing plant can be pre-defined and consequently time and costs are saved.

The present invention can also be employed in the screening of biomolecules and/or in the screening or formulations for particular biomolecules in order to determine, compare or improve biomolecules or formulations of biomolecules, which exhibit an improved tolerance against mechanical stress Accordingly, in one embodiment, the method of the present invention further comprises the step of determining and comparing said maximum tolerable stress load for the same biomolecule in different fluidic formulations. It has been found that optimizing the fluidic composition in which the biomolecules are dispersed., e.g. with respect to pH value, presence or absence of salt ions, surfactants or sugars, etc., can effectively improve mechanical stress tolerance of the biomolecules.

According to another embodiment, the method of the invention comprises the step of determining and comparing said maximum tolerable stress load for different biomolecules in the same fluidic formulation. It has also been found that certain structural elements of biomolecules strongly influence the mechanical stress tolerance. E.g. in proteins the number or arrangement of secondary structural elements such as alpha helices, beta sheets influence the stress tolerance of the protein. In particular, it has been found increasing molecular weight reduces stress tolerance while the an increasing number of disulfide bonds increases stress tolerance. It has therefore surprisingly been found that the ratio of the number of disulfide bonds to the molecular weight of the protein expressed in kDa correlates well with the stability of the protein against mechanical stress, i.e. the higher this ratio, the more stable will the protein be against mechanical stress.

It has been found that interfaces, such as surfaces of ducts, pipes and filters, which come into contact with the biomolecules-containing solution, may have an effect on the aggregation/degradation of the biomolecules. For instance, it has been observed that adherence of biomolecules to certain surfaces may influence the effects of mechanically stress on the biomolecules. In order to determine such effects, the method of the present invention preferably comprises the step of changing one or more interfaces contacting said fluid and determining the influence of said interfaces on the state of said particles. For instance, aggregate size distribution or bio-activity of the biomolecules could be effected by different surfaces. Accordingly, the device of the present invention preferably comprises components which are interchangeable. For instance, the rolls and/or the lid and/or the jacket of the device could be interchanged with similar components having at least a surface which is made from a different material. Also, components having different surface structure, e.g. different roughness, can be investigated with the device of the present invention. Also, as noted above, a gas space can be provided between the liquid surface and the lid in order to determine the influence of different liquid/gas interfaces on the aggregation/degradation of biomolecules.

DETAILED DESCRIPTION OF THE INVENTION

Figure 1:
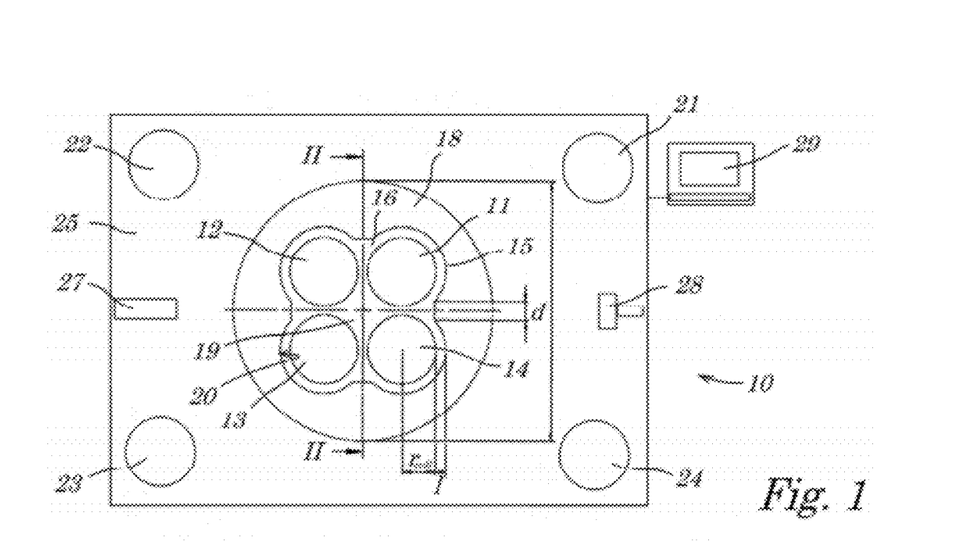
FIG. 1 is schematic plan view of an embodiment of the device of the present invention.

FIG. 1 is schematic plan view of an embodiment of the device of the present invention which is specially designed for determining the degradation and/or loss of activity of proteins and antibodies dispersed in a fluid under mechanical stress.

The device 10 of FIG. 1 comprises four cylindrical rolls 11, 12, 13, 14 rotatably arranged within a jacket 15 defining a sample chamber 16 of a housing 18. The rolls 11, 12, 13, 14 are arranged in square configuration such that a sample space 19 is defined between said rolls. The jacket has an inner surface 20 which is essentially adapted to the outer surface of the rolls in order to assume an essentially cloverleaf configuration in order to minimize sample volume and to eliminate dead spots in the fluid pattern. As can be taken from the drawing, each section of the jacket 15 adjacent to a roll has the shape of a circular arc extending over an angular range of approximately 180°. The four circular arcs are connected via short linear segments of the jacket.

Figure 2:
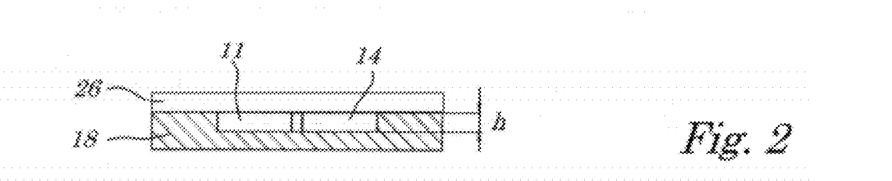
FIG. 2 is a cross-sectional view of the device of FIG. 1 along the line II-II of FIG. 1.

Each roll has a radius r of 10.5 mm and a height h of 5 mm which essentially corresponds to the height of the chamber 16 (c.f. FIG. 2). The gap l between each roll and the adjacent circular arc of the inner surface 20 of the jacket 15 is approximately 3 mm. The short linear segments of the jacket connecting the circular arcs have a length d of approximately 6 mm Accordingly, the total sample volume which can be house in the device of FIG. 1 is approximately 4.5 ml.

The jacket and the rolls are made of stainless steel (X10CrNiTi18.9) coated by a black perfluoroalkoxy (PFA) layer to guarantee good protein compatibility. The black color of the surface coating will help to minimize reflections during allows in-situ measurements. As a matter of course, other materials can be used as well (c.f. example 2 below).

Each roll 11, 12, 13 and 14 is independently driven by a separate geared motor 21, 22, 23, 24 arranged on a base plate 25 of the housing 18, which can be operated up to a rotational speed of up to 300 rpm. The speed transformation results from gear belts and the applied voltage. The range of the rotational speed can be varied by different gear belts, gearwheels and motors. The rolls are sealed by ball bearings (W608-2RS1, NiRo steel with NBR seal).

As can be taken from the cross sectional view of FIG. 2, the sample space my be sealed by a lid 26 to avoid adsorption phenomena of proteins at air/liquid interfaces. The lid can be designed to establish a head space above the sample volume which may be evacuated or filled with gases such as nitrogen, argon, filtered air, etc, in order to determine the influence of the liquid/gas interface on the behavior of biomolecules. Alternatively, the lid may be in contact with the sample liquid. In these cases, different lids made of different materials may be employed to determine effects of these materials on the results. Similarly, rolls 11, 12, 13 and 14 made from or coated with different materials may be employed for this purpose.

At one side of the jacket a light source 27 is arranged which allows to transmit light (e.g. UV light) through an optical window arranged in the jacket 15 through the sample space 19. The light irradiated light can leave the sample space 19 via an optical window arranged on the opposite side of the jacket and can be detected via a detector 28. Alternatively, optical fibers, e.g. for fluorescence measurements, terminating in the inner wall of the jacket or in the lid can be employed.

The operation of motors 21, 22, 23 and 24 to impart mechanical stress on the fluid as well as the acquisition of measurement data is controlled via a computer 29.

With the device of FIGS. 1 and 2, a specific Reynolds number can be defined as followed:

$$Re = \frac{\omega \cdot r \cdot l}{v}$$

In the equation ω is the angular velocity, r is the radius of the roll, l the size of the gap between roll and wall and v the kinematic viscosity of the fluid.

Example 1

Characterization of Flow Patterns

Figure 3A:
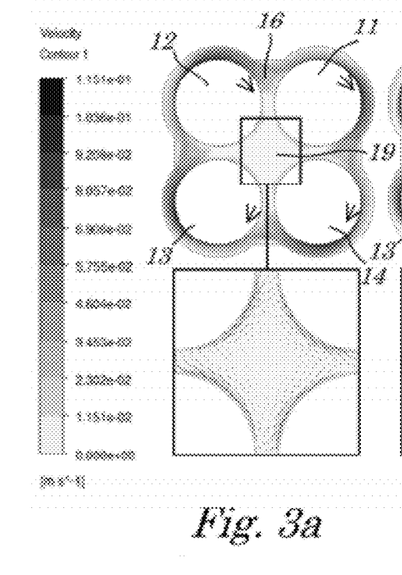
FIG. 3a-3c show a CFD simulation of three distinct flow patterns obtained by rotating the rolls of the device of FIG. 1 in three distinct modes.
Figures 3B, 3C:
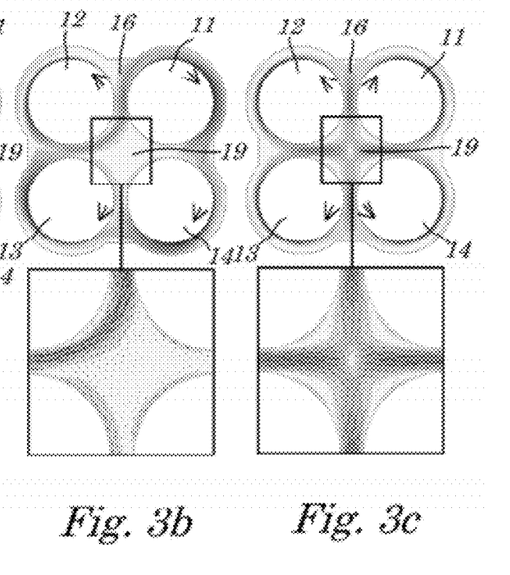

In FIGS. 3a, 3b and 3b three distinct flow patterns obtained by operating the device of FIG. 1 in three selected modes are shown. These results were obtained with Computational Fluid Dynamics (CFD) methods using water (Re 155) as a sample liquid (see also Example 1 below). Arrows indicate the rotation direction of the rolls. The upper drawing in each figure shows the rotation of the roll and a visualization of the flow pattern in the sample chamber 16. The lower drawings show an enlarged view of the flow pattern in the sample space 19 in the center of the chamber 16. In the case of FIG. 3*a*, all four rolls 11, 12, 13, 14 are rotated in the same direction with essentially the same angular speed. Accordingly, rotational stress is predominately imparted on particles in the sample space 19. In the case of FIG. 3*b*, a hybrid mode in employed where shear stress but also extensional stress and rotational stress is imparted on the particles by rotating one roll (e.g. roll 12 in FIG. 3*b*) in one direction and the two adjacent rolls (rolls 11 and 13) as well as the diagonally opposing roll (roll 14) in opposite directions. In FIG. 3*c*, extensional stress is exerted on the particles by rotating all four rolls such that each neighboring rolls are rotated in opposite directions. In the embodiment of FIG. 3*c*, rolls 11 and 13 are rotated clockwise while rolls 12 and 14 are rotated counter-clockwise.

It is known for instance from R. R. Lagnado, L. G. Leal, *Visualization of three-dimensional flow in a four-roll mill*, Experiments in fluids 9, 25-32 (1990), that there exists a break down of extensional flows in four-roll mills at a critical rotational speed. As the break down depends on the geometry, an extensive analysis of the flow pattern in the device of the present invention has been performed. The flow pattern of the device of FIG. 1 has been analyzed experimentally using Particle Image Velocimetry (PIV) and the experimental results have been compared with a numerical simulation of the device using Computational Fluid Dynamics (CFD).

Figures 3D, 3E, 4A:
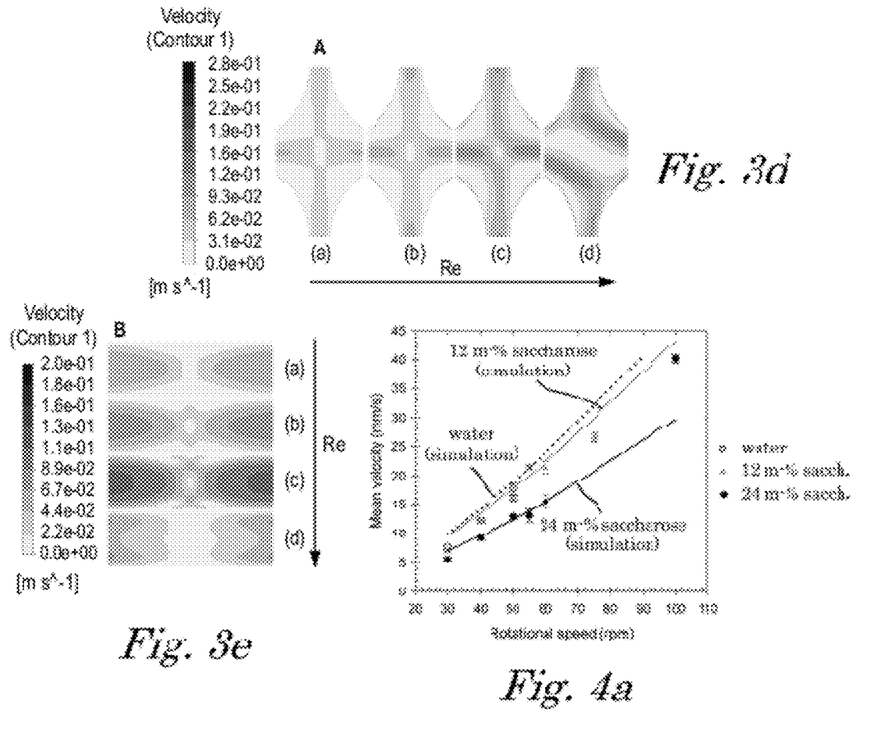
FIGS. 3d, 3e show top and side views, respectively, of a CFD simulation of the shrinking stagnation point and the break-up of extensional flow Reynolds number.
FIG. 4a is a comparison of experimentally and numerically obtained mean velocities in the central part of the four roll device of FIG. 1.

FIGS. 3*d* and 3*e* show a CH) simulation of the shrinking stagnation point and the break-up of extensional flow (c.f. also FIG. 3*c*) with increasing Reynolds number. FIG. 3*d* is a top view and FIG. 3*e* is side view of the centre plane. In both figures, diagram (a) corresponds to Re 194; (b) to Re 233; (c) to Re 349 and (d) to Re 388, respectively.

Particle velocities of the flow pattern for different Reynold numbers have been obtained for the fluids listed in Table 1 below.

TABLE 1

Material properties of the fluids used for PIV and CFD(T = 25° C.)

| fluid | viscosity [mPas] (experiment) | density [kg/m$^3$] (literature) |
|---|---|---|
| water | 0.85 | 997 |
| 12 m-% sucrose | 1.1 | 1046 |
| 24 m-% sucrose | 1.83 | 1107 |

The experimental results have been obtained using a measurement plane (dimension of 24 mm×12 mm×2 mm in the centre of the device) obtained by irradiating laser light into the plane and by focusing a CCD camera arranged above the centre of the device onto the desired layer.

At Re=58, a laminar extensional flow has been observed. With increasing Reynolds number the stagnation point in the centre shrunk and at Re=311 the extensional flow broke down. The break down of the flow pattern has been determined by analyzing the vector plots and quantitatively by plotting the velocity of a reference line in the centre of the four-roll mill By comparison of the vector plots and average velocities on the line the break down has been correlated with the decrease in the average velocity on the reference line. It has been confirmed that the higher the fluid viscosity was, the higher critical rotational speed that lead to break down has been achieved. Further, is has been confirmed that the higher the rotational speed of the rolls hand hence the Reynolds number has been, the higher was the flow velocity in the measurement plane. The results obtained for the different fluids suit well in the range of Reynolds numbers from 55 to 185. At higher Reynolds numbers there are higher deviations between the sugar solutions.

In order to verify the experimental analysis, the flow pattern in the four-roll device of FIG. 1 was calculated by using computational fluid dynamic software (ANSYS CFX10.0). The basis for the calculation is an extensive validated tetrahedral grid. It has been confirmed that the development of fluid flow in the simulation is similar to the experimental results. At low Reynolds numbers (Re=58) a laminar extensional flow is established. At Re=194 the stagnation point in the centre shrinks and with a further increase in Reynolds number the fluid flow breaks down. The break down of the flow appears to occur at slightly lower Reynolds numbers compared to the experimental investigation. The maximum of deviation between experiment and simulation is 26.5%. The experimental results and the computational results are summarized in table 2:

TABLE 2

Break down of extensional flow

| fluid | $Re_{break\,down}$ (experiment) [—] | $Re_{break\,down}$ (simulation) [—] | deviation [%] |
|---|---|---|---|
| water | 177 | 141 | 20 |
| 12 m-% sucrose | 291 | 214 | 26.5 |
| 24 m-% sucrose | 303 | 223 | 26 |

FIG. 4*a* shows a comparison of experimentally and numerically obtained mean flow velocities in the central part (12 mm×24 mm×5 mm) of the four roll device of FIG. 1 for three different Newtonian fluids (24 wt-% sucrose solution, 12 wt-% sucrose solution and 0 wt-% sucrose solution, i.e. pure water) in extension flow mode. Lines represent calculated data by CFD and symbols represent data obtained experimentally by PIV. The calculated values by the simulation are averaged over the measurement plane given in the experiments. As can been seen in the drawing, the results fit well together up to rotational speeds of 75 rpm.

Figure 4B:
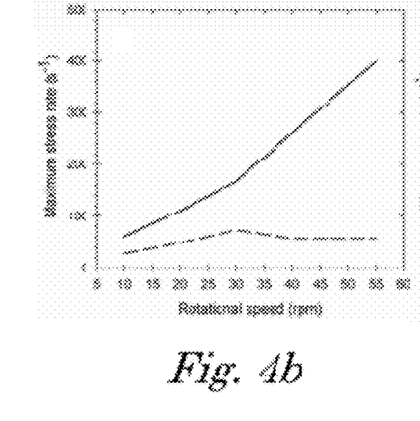
FIGS. 4b, 4c show maximum and mean stress rates for different rotational speeds of the rolls the device of FIG. 1.
Figure 4C:
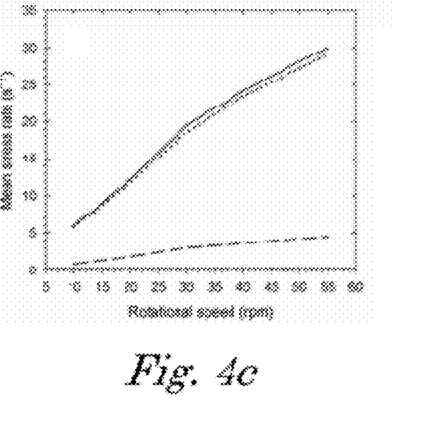

In FIGS. 4*b* and 4*c*, the maximum (FIG. 4*b*) and mean (FIG. 4*c*) shear, shear strain and extensional stress rates for different rotational speeds of the rolls with extensional flow mode using water as fluid in the four-roll device of FIG. 1 are shown. In the drawings, a continuous line (-) represents shear strain rate, a doted lined ( • • • ) shear stress rate and a dashed line ( - - - ) the extensional stress rate.

Example 2

Aggregation of a Monoclonal Antibody Fragment

One form of protein degradation that may be induced by mechanical stress is the formation of large aggregates. Different external effects such as high temperature, extreme pH values, high salt concentrations, adsorption phenomena and mechanical stress can lead to changes in structure and/or aggregation of proteins. In this example, the aggregation of a monoclonal antibody fragment has been investigated.

The formation of aggregates during the development and production of therapeutic proteins in biopharmaceutical industries is problematic as this can lead to an inactivation of the molecules and to immune response of the organism. Protein aggregates can be formed due to the above mentioned external effects or under physiological conditions (neutral pH, T=37° C.). They include mainly non-native intermolecular β-sheets, independent of the native structure or the aggregate morphology (amorphous or fibrous).

For many proteins it was observed that the aggregation mechanism is a first order reaction. That means that the reaction determining step is unimolecular, hence a conformational change occurs and the mechanism is not determined by collision frequencies. For some proteins a reaction of second order was observed. Two native molecules aggregate due to an irreversible reaction to a dimer. Due to these models it is obvious that protein aggregation is influenced by the intrinsic stability of the proteins that determines the transition to a thermodynamically unstable state and/or by the colloidal stability. The stability of the native protein and the colloidal stability (intermolecular interactions) are strongly influenced by the environment of the protein. An important role plays the pH value which affects the overall charge of the molecules but also added buffer ions, salts, surfactants, sugar, etc.

The size of protein aggregates which are formed due to mechanical stress is broad from the nanometer range up to approximately 50 micrometer. This results in high requirements on the analytical techniques and it is essential to use different methods (size exclusion chromatography, turbidity, single particle counting, dynamic light scattering, light microscopy, flow field fractionation, etc.).

The colloidal stability of different formulations was measured and aggregation tests were performed. The intermolecular interactions were determined by measuring the zetapotential and the concentration dependency of the diffusion coefficient. In general the zetapotential is a quantity for the overall net charge of the molecules and therefore for the electrostatic interactions. It is strongly influenced by the pH value which causes the protonation and de-protonation of the amino acids. Added salt ions screen the charge of the molecules and this leads to a decrease in zetapotential.

Figure 5:
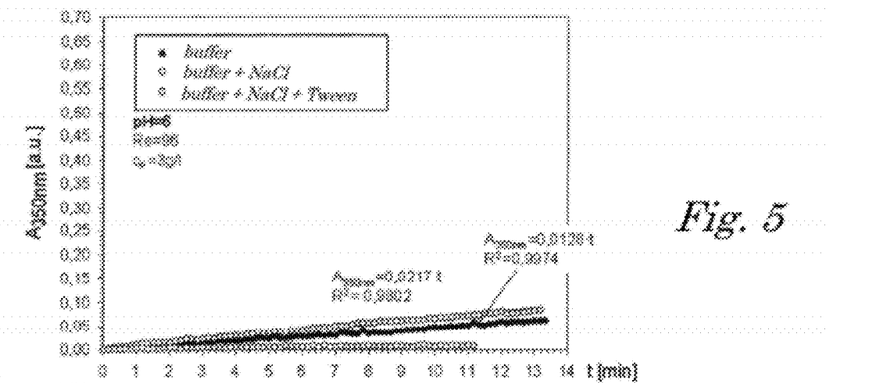
FIG. 5 depicts in-situ absorption measurements of a monoclonal antibody fragment in an extensional flow field in the device of FIG. 1 at pH 6.

The overall interaction potential of proteins is influenced in addition to electrostatic interactions by many further interactions (xDLVO) and can be measured by the second virial coefficient $B_{22}$ and/or the interaction parameter $k_D$ (concentration dependency of the diffusion coefficient). For the antibody fragment the $K_D$-values change with the pH value. Independent of added salt ions, the interaction parameter increases at pH 7 which results in more attractive interactions. It can be observed that the charge of the protein molecules play a dominant role with regard to intermolecular interactions. FIG. 5 depicts in-situ absorption measurements of the monoclonal antibody fragment mAb1 in an extensional flow field in the device of FIG. 1 at pH 6. It is evident, that aggregation behavior of the monoclonal antibody fragment is influenced the formulations (buffer, buffer+NaCL, buffer+NaCl+Polysorbate 80 (Tween80)) during aggregation tests in the four-roll device. In-situ absorption measurements enable time resolved detection of aggregation in fluid flows. The absorption of light of wavelength 350 nm is caused by Mie scattering of formed aggregates larger than 350 nm.

Figure 6:
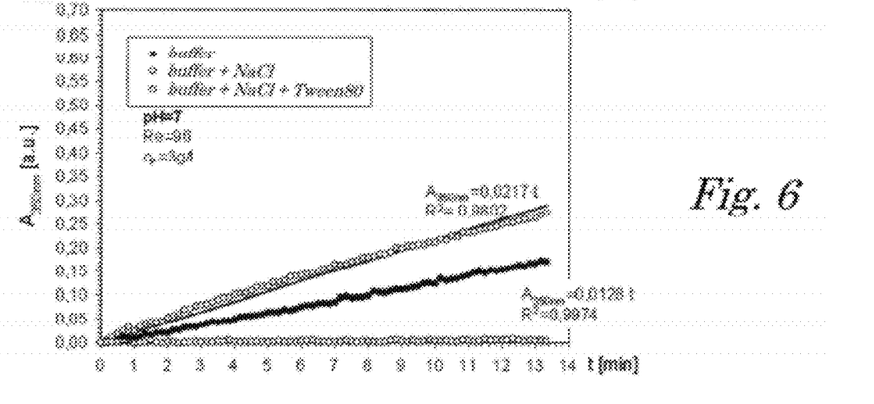
FIG. 6 depicts in-situ absorption measurements of a monoclonal antibody fragment in an extensional flow field in the device of FIG. 1 at pH 7.

FIG. 6 depicts in-situ absorption measurements of a monoclonal antibody fragment mAb1 in an extensional flow field in the device of FIG. 1 at pH 7. As can be seen, the monoclonal antibody fragment forms more aggregates at pH 7 in buffer and in buffer with added NaCl than at pH 6. While the stability at pH 6 is comparable in buffer and in buffer with added NaCl, differences in the aggregation behavior can be detected. This can be explained by conformational changes of the protein in the formulation with added NaCl at pH 7.

Figure 7:
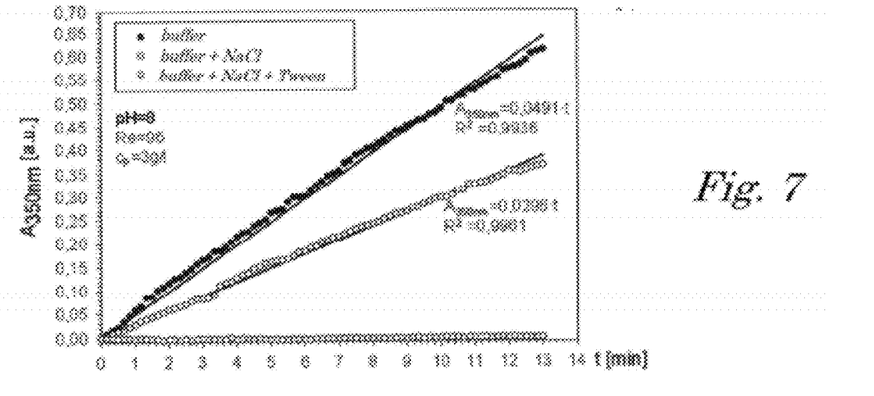
FIG. 7 depicts in-situ absorption measurements of a monoclonal antibody fragment in an extensional flow field in the device of FIG. 1 at pH 8.

As can be taken from FIG. 7, which depicts a similar in-situ absorption measurements at pH 8, the aggregation increases at pH 8 even more. Addition of Polysorbate 80 decreases, independent of the pH value, the antibody aggregation.

Figure 8:
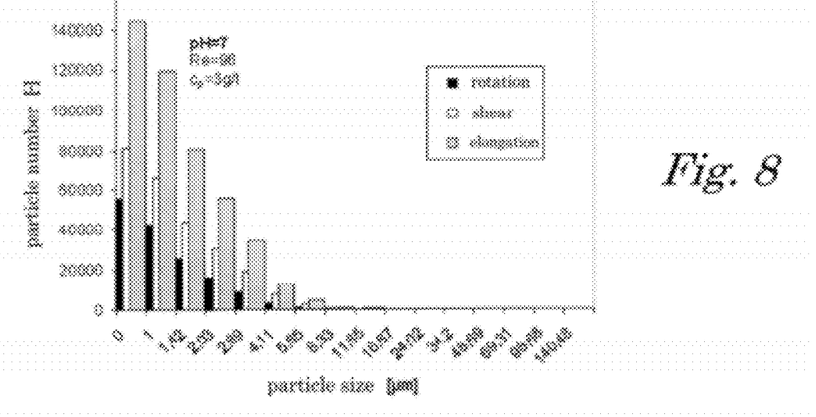
FIG. 8 is a diagram showing aggregate formation of a monoclonal antibody fragment in different flow patterns measured by light blockage.

In addition to the changing formulation additives, the influence of the particular type of flow has on aggregation behaviour has been investigated. FIG. 8 is a diagram showing aggregate formation of the monoclonal antibody fragment mAb1 in different flow patterns measured by light blockage. As can be seen, the mechanical stress in the extensional flow leads to the largest amount of aggregates. Shear forces have at same Reynolds numbers a lower influence and in rotational flow the lowest number of aggregates was detected.

The results of the aggregation studies show that the in-situ measurement of absorption with glass fibres can be used to detect formed aggregates in fluid flows. Furthermore first results show that at constant Reynolds numbers extensional forces have a stronger influence with regard to aggregation compared to shear and rotation.

As antibody aggregation depends on the colloidal and intrinsic stability of the molecules, in-situ fluorescence spectroscopy may also be used for the detection of conformational changes (c.f. example 4 below).

Figure 9:
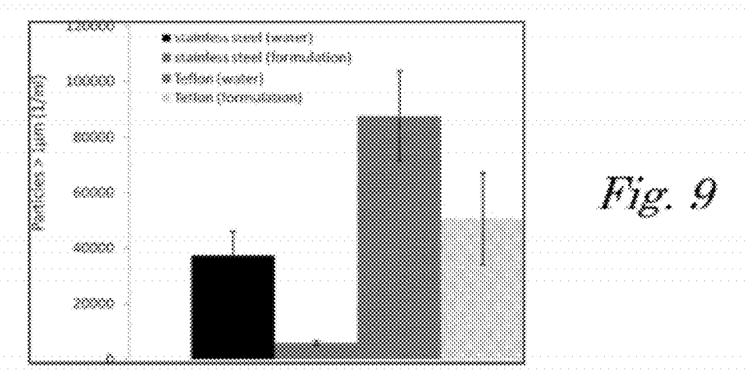
FIG. 9 shows the effect of roll material on the aggregate formation of a monoclonal antibody fragment.

It has also been determined that the material of the rolls may influence particle formation during stress. Accordingly, the device of the invention offers for instance the possibility to determine effects of different materials on protein aggregation and protein degradation in different processing environments. FIG. 9 depicts the number of particles larger than 1 micrometer for monoclonal antibody fragment A (mAb A) aggregates at pH 6 as measured by light blockage. The columns in FIG. 9 show from left to right stainless steel rolls in water, stainless steel rolls in formulation, polytetrafluoroethylene (PTFE) rolls in water and PTFE rolls in formulation, respectively. It is evident from FIG. 9 that the PTFE rolls result in a larger number aggregates. Thus, it appears that protein aggregation and degradation is not only influenced by fluid dynamically induced mechanical stress but also by the interaction of the particles with surface materials. As shown in FIG. 9, the device of the present invention can also be used to determine whether certain formulations are beneficial in order to mitigate surface effects on biomolecule degradation by mechanical stress under certain process conditions.

The device of the present invention allows to easily interchange between components such as rolls, lids etc. made from different materials. Thus the device of the invention can be used to distinguish between material-induced effects and fluid dynamically induced effects and to optimize process condition accordingly.

Figure 10:
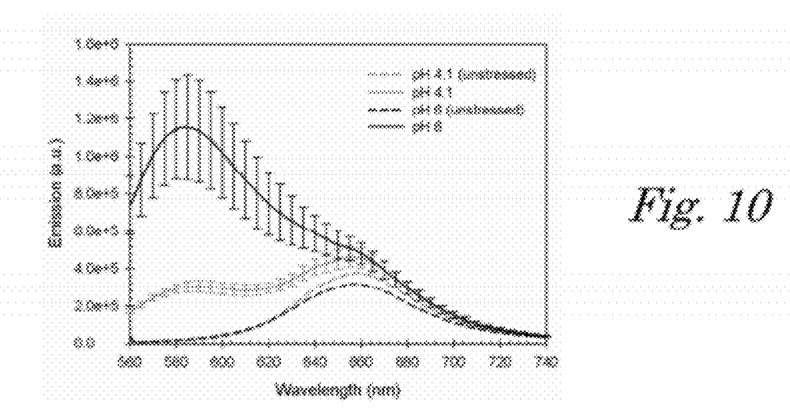
FIG. 10 shows results of fluorescence measurements in mechanically stressed and unstressed monoclonal antibody fragments.
Figure 11:
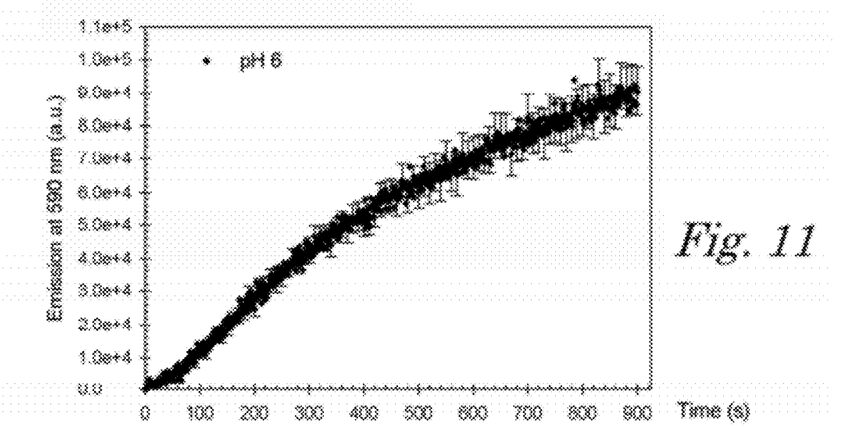
FIG. 11 shows fluorescence changes while mechanically stressing of a monoclonal antibody fragment.

In the device of the present invention a variety of analytical tools, such as light extinction measurements, UV/VIS spectroscopy or fluorescence spectroscopy, can be employed to monitor protein aggregation and degradation while imparting mechanical stress on the particles. As far as fluorescence measurements are concerned, intrinsic fluorescence of proteins (e.g. tryptophan fluorescence) can be used. However, intensity changes in the fluorescence spectrum can be influenced by scattering effects of formed aggregates. Therefore, in many application of the four-roll device of the invention, it is preferred to use extrinsic fluorescence dyes. Such dyes allow to determine structural changes of proteins (e.g. exposure of certain chemical groups of the protein). As an example, FIG. 10 depicts fluorescence spectra of a mechanically stressed and unstressed mAb A solution (0.1 g/l) at pH 6 and pH 4. An extrinsic fluorescence dye (Nile red, 5 µM, excitation at 550 nm) has been used. As can be taken from FIG. 10, mechanical stress results in a significantly increased fluorescence between 560 nm and 660 nm. Is further confirmed by FIG. 11 which shows an in situ measurement of the variation of Nile red (5 μM, excitation 550 nm) fluorescence at 590 nm in time while stressing a mAb A solution at pH 6. It has been confirmed that agglomeration of the antibody fragment is associated with structural changes, namely the exposure of hydrophilic groups.

Example 3

Deactivation of Lysozyme

Degradation of proteins due to mechanical stress may also result in a loss of activity of proteins. Activity loss may be induced by structural changes and/or aggregation. The measurement of the activity loss is therefore a helpful method to quantify the degradation.

In the present example the activity loss of lysozyme has been determined upon mechanical stress imparted on a lysozyme solution using the device of FIG. 1.

Figure 12:
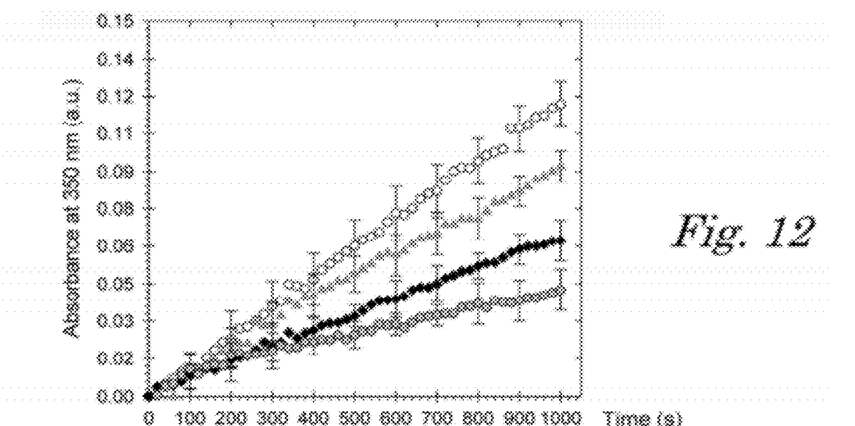
FIG. 12 shows in situ turbidity measurements at 350 nm during stressing of lysozyme at different rotational speeds in extensional flow mode.

FIG. 12 shows in situ turbidity (absorbance) measurements at 350 nm during stressing of lysozyme at different rotational speeds in extensional flow mode with the device of FIG. 1 using PTFE rolls and PTFE lid. Rotational speeds are indicated by different bullets in FIG. 12, i.e. ○ corresponds to 55 rpm, ▲ to 45 rpm, ■ to 35 rpm and ▲ to 25 rpm. Generally, absorbance increase with both rotational speed and impact duration of the mechanical stress.

Figure 13:
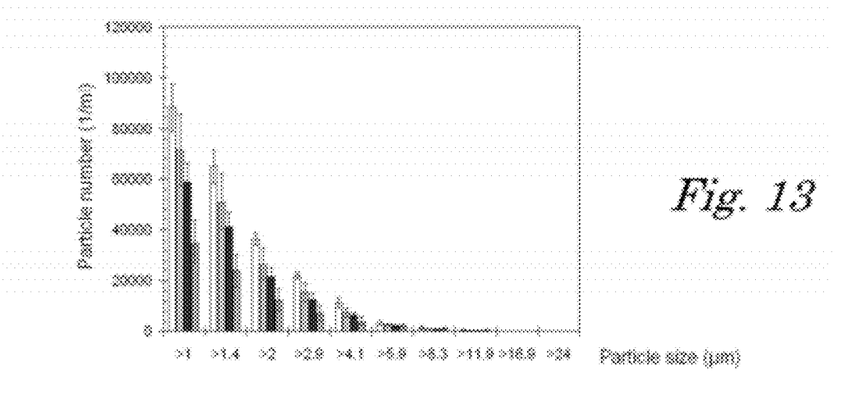
FIG. 13 shows particle size distribution after stressing of lysozyme at different rotational speeds in extensional flow mode.

This is also verified by the measured particles size distribution after stressing. FIG. 13 shows the results of lysozyme at different rotational speeds in extensional flow mode with the device of FIG. 1 using PTFE rolls and PTFE lid. In each sub-group, four columns indicate different rotational speeds, namely, from left to right: white column: 55 rpm; grey column: 45 rpm; black column: 35 rpm and shaded column: 25 rpm.

Figure 14:
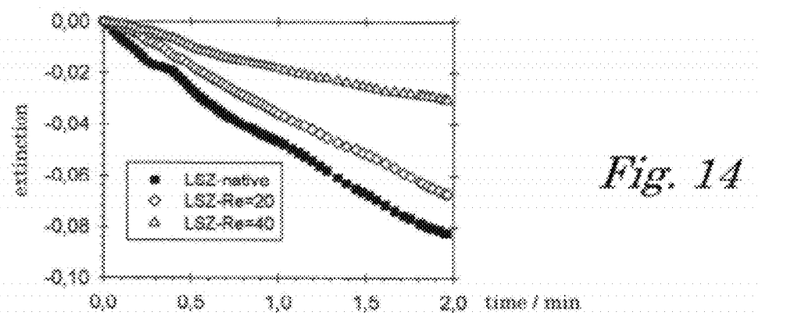
FIG. 14 visualizes the determination of lysozyme activity.
Figure 15:
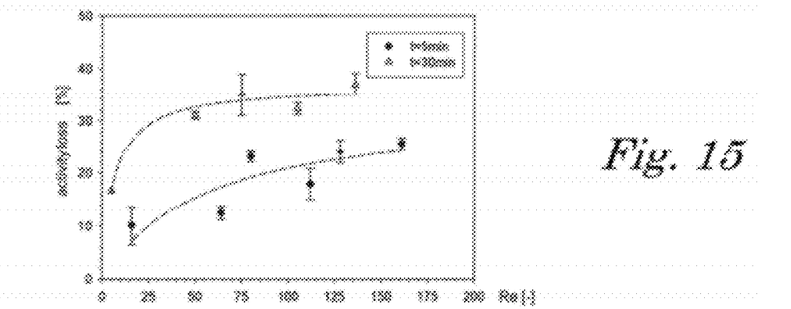
FIG. 15 depicts the activity loss of lysozyme in extensional flows as a function of Reynolds number and the impact time in the device of FIG. 1.

As can be taken form FIG. 14, lysozyme activity $A_v$ can be determined from extinction measurements at 350 nm during lysis of *Micrococcus lysodeikticus* according to the equation $$A_v = \frac{m}{k \cdot V_S}$$

where $V_S$ is the sample volume, k is a constant (0.001/min) and m is the gradient of the linear regression in the plot of FIG. 14. As can be taken from the extinction measurement directly, lysozyme activity decreases with increasing mechanical impact (increasing Reynolds number). This result has been summarized in FIG. 15 which depicts the activity loss of lysozyme in extensional flows as a function of Reynolds number and the impact time. As can bee seen, the impact intensity that acts on the molecules is in addition to the Reynolds number strongly influenced by the impact time.

Figure 16:
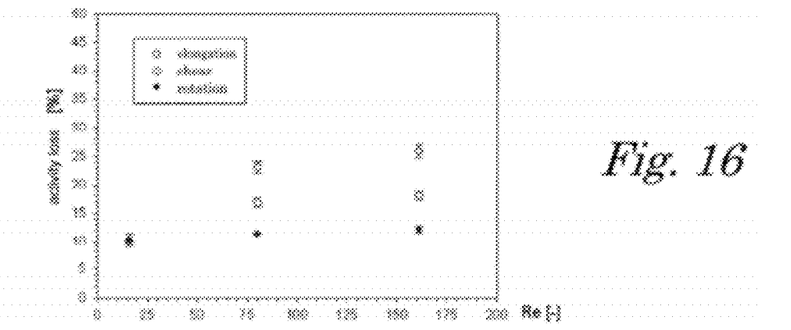
FIG. 16 depicts the activity loss of lysozyme as a function of the flow pattern and Reynolds number in the device of FIG. 1.

Further, as can be taken from FIG. 16 which depicts the activity loss of lysozyme as a function of the flow pattern and Reynolds number in the device of FIG. 1, the type of mechanical stress does also influence lysozyme activity. Extensional forces appear to have a stronger influence on the activity loss of proteins. Shear forces have a lower effect and effects of rotational forces appear to be weak.

Light scattering investigations reveal that the activity loss of lysozyme is at least partly associated with aggregate formation. Lysozyme aggregates formed by mechanical stress will predominately scatter light in the Mie scattering regime.

Figure 17:
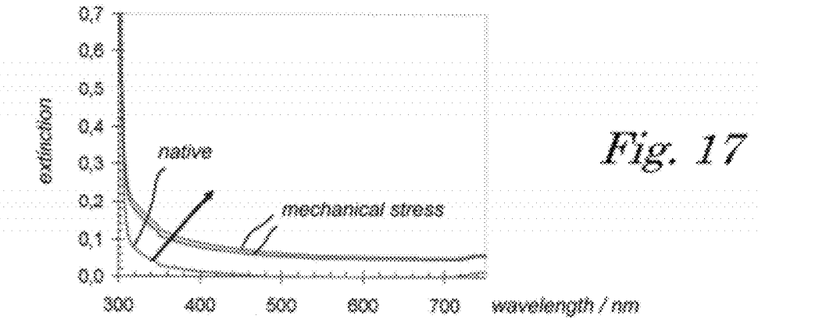
FIG. 17 depicts changes in the UV/VIS spectrum of lysozyme caused by mechanical stress.

In the UV/VIS spectrum of FIG. 17, increased extinction by aggregate formation due to stress impact is clearly visible.

Figure 18:
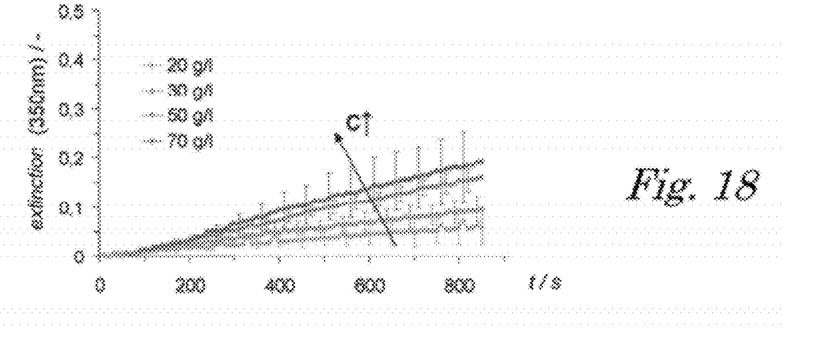
FIG. 18 shows the dependence of lysozyme aggregate formation on lysozyme concentration as determined by UV/VIS spectroscopy.
Figure 19:
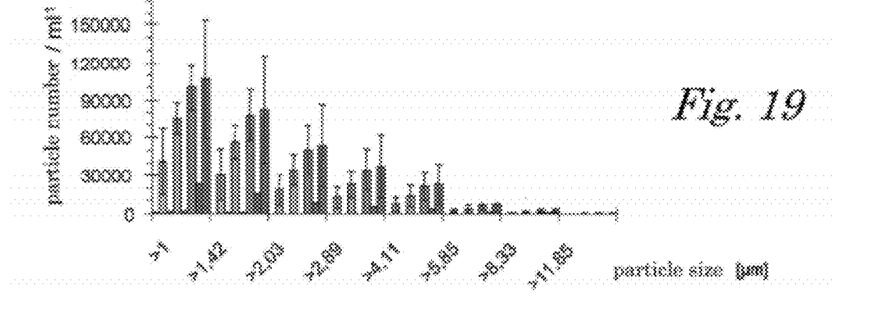
FIG. 19 shows a dependence of lysozyme aggregate formation on lysozyme concentration as determined by particle counting.

Further, concentration dependence of aggregate formation has been investigated. FIG. 18 shows the dependence of lysozyme aggregate formation on lysozyme concentration as determined by UV/VIS spectroscopy. Lysozyme was dissolved in water at pH 5.1. An extensional stress at Re=128 was imparted on the on the protein solution using the device of FIG. 1. Protein concentration varied between 20 g/l and 70 g/l. As can be seen, at the same mechanical stress impact, the formation of aggregates larger that 1 micron increases with increasing protein concentration. This result has been confirmed by light blockage measurements. FIG. 19 shows the corresponding particle numbers for certain size ranges. In each size range of FIG. 19, four columns pairs are depicted corresponding to the four protein concentration of FIG. 18 (i.e, form left to right, 20 g/l, 30 g/l, 50 g/l, 70 g/l). Each column pair consists of a column for the native protein solution (left) and one column for the stressed protein solution (right). As can be seen the results obtained by particle counting correspond to the US/VIS data.

Figure 20:
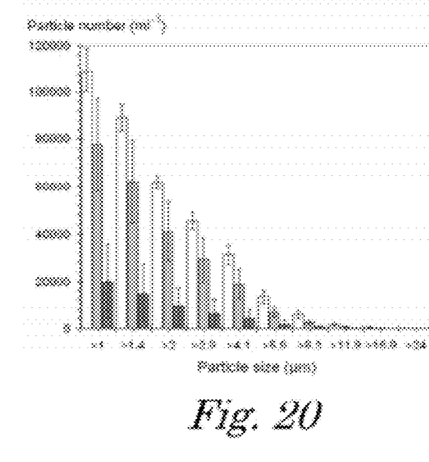
FIG. 20 shows the influence of different flow profiles (extensional, hybrid (shear) and rotational stress) on particle size distribution of lysozyme.

As described above in connection with FIGS. 3a-3e, the device of the present invention allows to impart distinct flow filed pattern and consequently distinct stress loads on particles in a fluid. Consequently, it is possible to use the device of the invention to distinguish the influence of different types of mechanical stress on protein aggregation and degradation. FIG. 20 depicts the measured particles sizes after stressing of lysozyme in different flow profiles (extension, hybrid and rotation) at constant rotational speed of 40 rpm with the device of FIG. 1 using PTFE rolls and a PTFE lid. Columns in each sub-group present different flow profiles and consequently different mechanical stress load, namely: white column: extensional stress; grey column: hybrid stress and shaded column: rotational stress.

Figure 21:
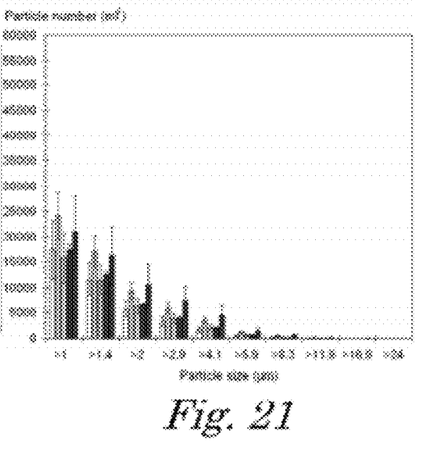
FIG. 21 shows the influence of different lid materials and contact times before stressing was performed on particle size distribution of lysozyme.

As noted above, surface effects may influence the measured results. In FIG. 21, the measured particle size distribution after stressing of lysozyme in extensional flow (5 min at 20 rpm) is depicted. Before stress was imparted on the particle solution, the solution was allowed to contact the lid for a certain amount of time. Different lid materials and different contact times were used. The columns in each sub-group of FIG. 21 represent from left to right: white column: no lid for 5 s; shaded column: acrylic glass lid for 5 s; grey column: PTFE lid for 5 s; black/white dotted column: stainless steel rollers; black column: PTFE lid for 30 min.

Example 4

Influence of Protein Structure on Mechanical Stress Tolerance of Proteins

As outlined above, the method and the device of the present invention may also be used to optimize protein structures in terms of increasing tolerance against mechanical stress. In the present example, stress effects on various proteins (namely lysozyme (LSZ), ribonuclease A (RNase A), bovine serum albumin (BSA), phospholipase A2 ($PLA_2$) and alcohol dehydrogenases (ADH) have been investigated. The results have been correlated with structural properties of the proteins such as molecular weight, the number of alpha helices, the number of beta sheets and the number of disulfide bonds.

Similar conditions for the proteins have been established ($K_D$=0.004 l/g, protein concentration in water $c_P$=30 g/l). The protein solutions have been subjected to an extensional stress in the device of FIG. 1.

Figure 22:
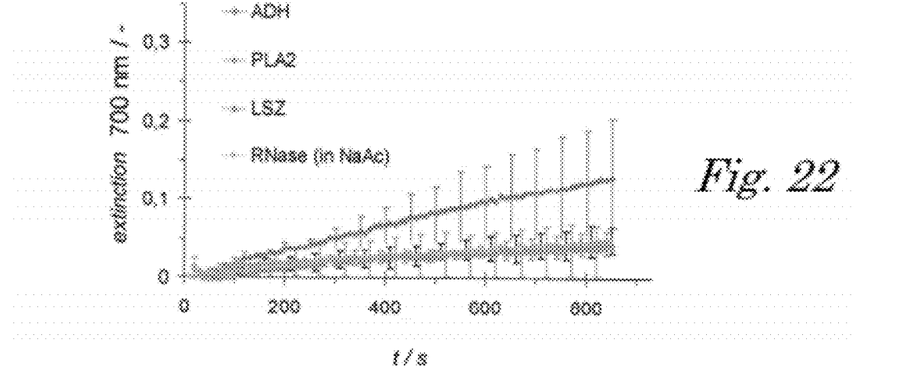
FIG. 22 shows the dependence of aggregate formation on protein structure as determined by in-situ UV/VIS spectroscopy.
Figure 23:
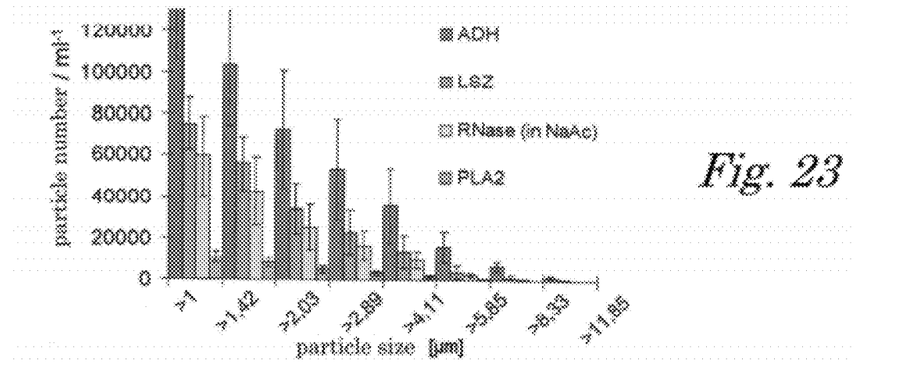
FIG. 23 shows the dependence of aggregate formation on protein structure as determined by particle counting.

FIG. 22 shows the dependence of aggregate formation on protein structure as determined by in-situ UV/VIS spectroscopy at a wavelength of 700 nm for four of the above mentioned proteins. The UV/VIS results have been verified by particle counting using light blockage techniques as depicted in FIG. 23. As can be taken from FIGS. 22 and 23 and even more clearly form particle counting, aggregation effects are smallest with PLA2, more prominent with RNase and LSZ and significantly strongest with ADH.

Figure 24:
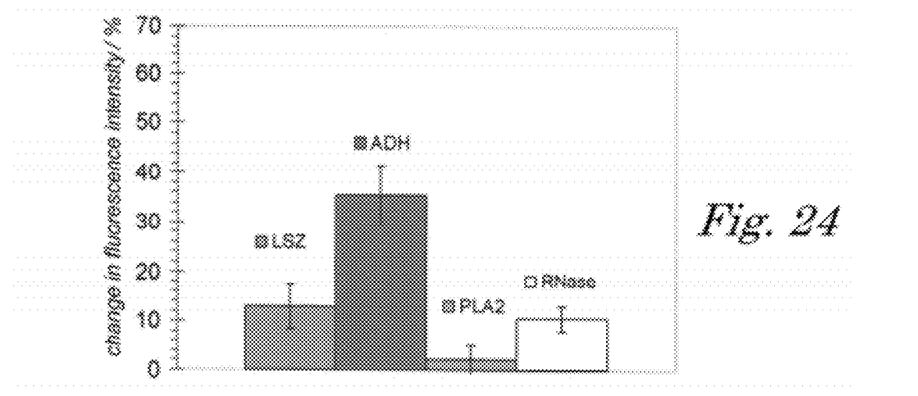
FIG. 24 shows the stress induced changes in tertiary protein structure for different proteins as determined by fluorescence spectroscopy.

Fluorescence spectroscopy has been employed to investigate structural changes via changes of the intrinsic fluorescence of the proteins. FIG. 24 shows the stress induced changes in tertiary protein structure for different proteins as determined by changes in intrinsic fluorescence. As can be seen, all proteins exhibit stress induced changes with ADH being again most prominent.

Figure 25:
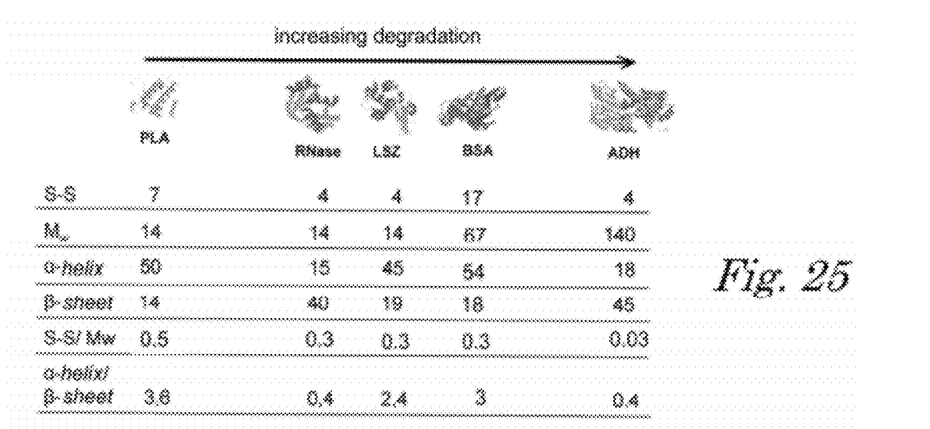
FIG. 25 visualizes a dependence of protein degradation on protein structure.

In FIG. 25 which summarized the results of various investigations, it can be seen that the ratio of the number of disulfide bonds to molecular weight expressed in kDa appears to be a suitable indicator of stress tolerance of the proteins. With these observations, protein design can be optimized.

Figure 26:
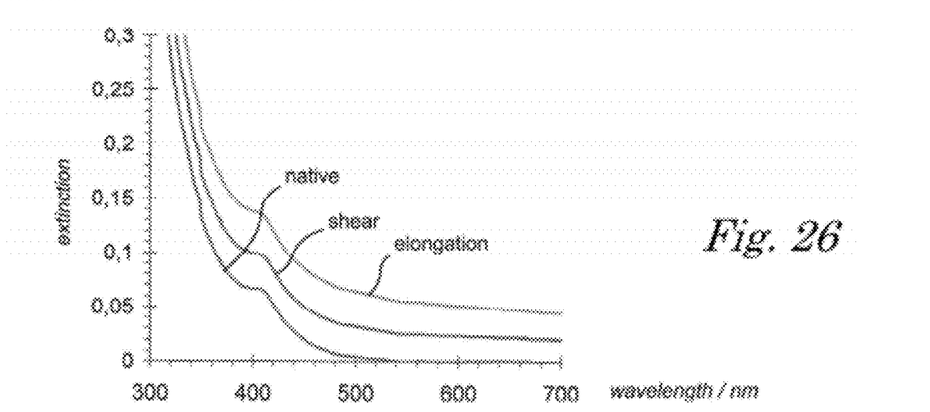
FIG. 26 depicts the influence of shear and extensional stress on protein degradation as determined by in-situ UV/VIS spectroscopy.
Figure 27:
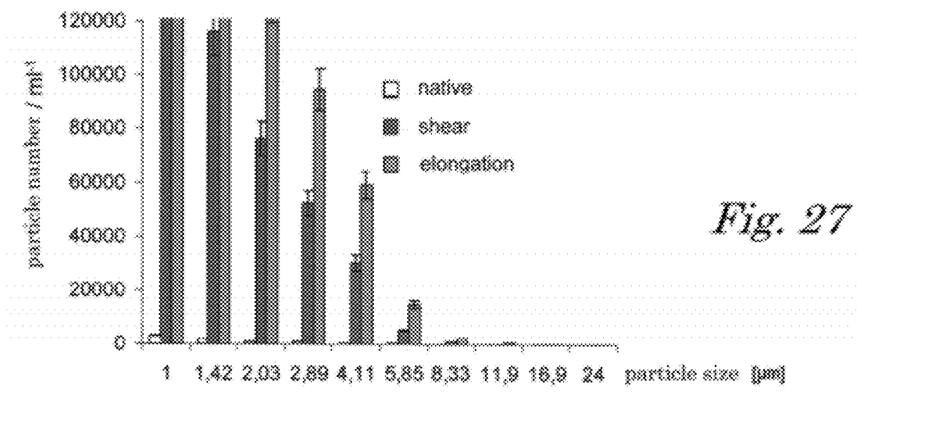
FIG. 27 depicts the influence of shear and extensional stress on protein degradation as determined by particle counting.

Finally, the influence of different types of stress in BSA has been investigated. An aqueous BSA solution at pH 6 and at a protein concentration has been subjected to shear stress and extensional stress, respectively at $\bar{\epsilon}=15/s$. FIG. 26 depicts results as determined by in-situ UV/VIS spectroscopy and FIG. 27 depicts the results as determined by particle counting (light blockage). As can be seen, extensional stress appears to have the strongest effect on protein degradation.

The invention claimed is:

1. Method for determining mechanical stress load on particles dispersed in a fluid, comprising the steps of
feeding fluid comprising dispersed particles into a sample space of a device comprising a jacket which encloses a sample chamber and at least two rolls arranged within said jacket such that said sample space is defined between said rolls, said rolls being independently rotatable with respect to each other, wherein said jacket has an inner surface which is essentially adapted to the outer surface of the rolls,
imparting rotational movement to at least one of the rolls of said device,
determining changes in the state of said particles.

2. The method of claim 1, wherein said fluid is continuously passed though said sample space.

3. The method of claim 1, wherein said fluid is fed into said sample space and said at least one roll is rotated for a predetermined time.

4. The method of claim 1, wherein said rolls are rotated so as to impart at least one of rotational stress, shear stress and extensional stress on said particles.

5. The method of claim 1, wherein said particles dispersed in said fluid comprise biomolecules.

6. The method of claim 1, further comprising the step of determining a maximum tolerable stress load of said biomolecules.

7. The method of claim 6, further comprising the step of determining and comparing said maximum tolerable stress load for the same biomolecule in different fluidic formulations.

8. Plant for processing biomolecules dispersed in fluids, wherein the formulation of the biomolecules in the fluid has been optimized for increased tolerable stress load using the method of claim 7.

9. The method of claim 6, further comprising the step of determining and comparing said maximum tolerable stress load for different biomolecules in the same fluidic formulation.

10. The method of claim 9, further comprising the step structurally optimizing said biomolecule, in particular a protein, for increase tolerable stress load, in particular extensional stress load.

11. Plant for processing biomolecules dispersed in fluids, wherein said biomolecules have been structurally optimized for increased tolerable stress load using the method of claim 9.

12. The method of claim 6, wherein tolerable extensional stress load is determined for a proteins.

13. Plant for processing biomolecules dispersed in fluids, wherein said plant is designed such that the stress load acting on said biomolecules does not exceed a maximum tolerable stress load as determined with the method of claim 6.

14. The method of claim 1, further comprising the step of changing one or more interfaces contacting said fluid and determining the influence of said interfaces on the state of said particles.

15. Device for determining mechanical stress load on particles dispersed in a fluid, comprising a jacket which encloses a sample chamber and at least two rolls arranged within said jacket such that a sample space is defined between said rolls, said rolls being independently rotatable with respect to each other, wherein said jacket has an inner surface which is essentially adapted to the outer surface of the rolls.

16. The device of claim 15, wherein said rolls are essentially cylindrical rolls having a first radius of curvature.

17. The device of claim 16, wherein said inner surface of said jacket comprises at least partially an essentially cylindrical shape having a second radius of curvature which is slightly larger than said first radius of curvature.

18. The device of claim 15, wherein four rolls are housed within said jacket.

19. The device of claim 15, further comprising means for determining changes in the state of said particles dispersed in said fluid.

20. The device of claim 19, wherein said means for determining changes in the state of said particles are arranged downstream of said sample space.

21. The device of claim 20, wherein said means for determining changes in the state of said particles are arranged such that said changes of the sate of said particles can be determined via online measurement within said sample space.

22. The device of claim 15, wherein said outer surfaces of said rolls and said inner surface of said jacket are biocompatible surfaces.

23. The device of claim 15, further comprising means for controlling the temperature of the sample space.

24. The device of claim 15, further comprising a lid for closing the sample space.

25. The device of claim 24, wherein said lid defines a gas space over said sample space.

26. The device of claim 15, wherein said device comprises interchangeable components.

* * * * *